United States Patent [19]
Auer et al.

[11] Patent Number: 5,367,474
[45] Date of Patent: Nov. 22, 1994

[54] FLOW CYTOMETER

[75] Inventors: Robert E. Auer, Miami; Bruce M. Weber, Cooper City; John D. Starling, Coral Gables; James C. S. Wood, Coral Springs, all of Fla.

[73] Assignee: Coulter Corporation, Miami, Fla.

[21] Appl. No.: 14,701

[22] Filed: Feb. 8, 1993

[51] Int. Cl.[5] ............................................. G01N 15/00
[52] U.S. Cl. .................................... 364/555; 356/317; 356/442; 364/413.08
[58] Field of Search ............... 209/576; 250/461.2; 356/39, 317, 318, 442; 364/555, 139, 177, 413.08; 340/825.06, 825.07, 825.08

[56] References Cited

U.S. PATENT DOCUMENTS

| | | | |
|---|---|---|---|
| 3,380,584 | 4/1968 | Fulwyler. | |
| 3,657,537 | 4/1972 | Wheeless, Jr.. | |
| 3,761,889 | 9/1973 | Hallee et al. | 340/172.5 |
| 3,818,200 | 6/1974 | Pilhofer | 235/151.3 |
| 3,923,397 | 12/1975 | Shuck | 356/204 |
| 4,038,556 | 7/1977 | Auer et al.. | |
| 4,348,107 | 9/1982 | Leif. | |
| 4,667,830 | 5/1987 | Nozake, Jr.. | |
| 4,778,593 | 10/1988 | Yamashita. | |
| 4,987,539 | 1/1991 | Moore et al. | 364/555 |
| 5,166,675 | 11/1992 | Amemiya et al. | 340/825.08 |

Primary Examiner—Jack B. Harvey
Assistant Examiner—Craig Steven Miller
Attorney, Agent, or Firm—John T. Winburn

[57] ABSTRACT

A flow cytometer includes a plurality of detectors for providing voltage pulse signals over a four decade range as particles pass through an illuminated detection station. Each voltage pulse signal is processed and provided to a first sample and hold for storage. Thereafter, the value in the first sample and hold is amplified by one or thirty-two, depending upon its magnitude, and stored in a second sample and hold for subsequent provision to a sixteen bit analog to digital convertor (ADC), one signal at a time. The first sample and hold is then free to store a new value while the old value is awaiting provision to the ADC. The ADC converts the signal received from the second sample and hold to a fifteen bit digital signal and uses the sixteenth bit to manifest whether the signal stored in the second sample and hold was amplified by thirty-two.

46 Claims, 8 Drawing Sheets

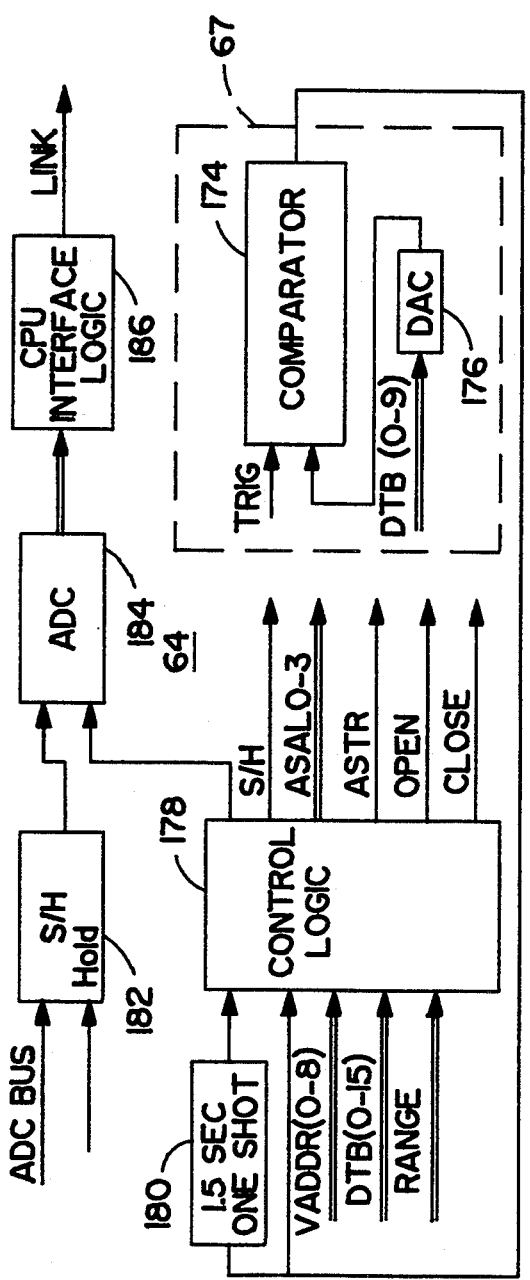
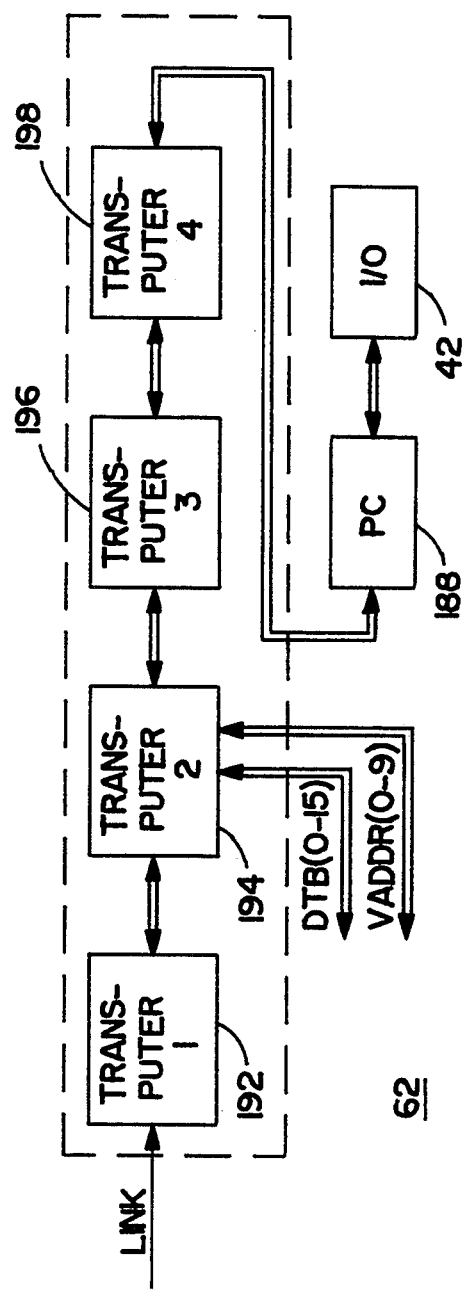

FLOW CYTOMETER

BACKGROUND OF THE INVENTION

1. Field Of The Invention

This invention relates to a flow cytometer, and more particularly, to a flow cytometer having the capability of processing signal voltages ranging over at least four orders of magnitude and for detecting new signals prior to completing the processing of previously detected signals.

2. Description of the Prior Art

Flow cytometer systems are common medical laboratory instruments used to perform an analysis of many different cell types, including blood cells. For example, they are commonly used to count and differentiate between various types of blood cells, particularly subtypes of white blood cells. Generally, conventional flow cytometer systems, utilize a narrow columnar stream of fluid formed to contain the cells to be examined. This stream passes through a flow cell having a window through which a light beam, such as from a laser, is passed. When a cell intersects the light beam, light is scattered in the forward direction which is proportional to the size of the cell, and at wide angles from the smaller structures of the cell. Generally, the cells being examined will previously have been treated with fluorescent dyes or markers connected to fluorescent dyes, and after being placed in the light path, different cells will emit different fluorescent color and intensity light patterns. Particular cells can be identified by observing both the effect of the light scattered from the cell, such as the amount of light scattered at various angles, as well as the various fluorescent light patterns.

Examples of various prior art flow cytometer systems are shown in U.S. Pat. No. 3,380,584 granted Apr. 30, 1968 to M. J. Fulwyler and entitled "Particle Separator"; U.S. Pat. No. 3,657,537, granted Apr. 18, 1972 in the name of L. L. Wheeless, Jr. et al and entitled, "Computerized Slit-Scan Cytofluorometer For Automated Cell Recognition"; U.S. Pat. No. 4,038,556 granted Jul. 26, 1977 in the name of Robert E. Auer et al and entitled, "Method and Apparatus For Simultaneous Optical Measurements of Particle Characteristics"; U.S. Pat. No. 4,348,107, granted Sep. 7, 1982 in the name of Robert C. Leif and entitled, "Orifice Inside Optical Element"; U.S. Pat. No. 4,467,830, granted May 26, 1987 in the name of Tom Nozaki, Jr. et al and entitled, "Method And Means For Sorting Individual Particles Into Containers For Culturing, Cloning Analysis Or The Like"; and U.S. Pat. No. 4,778,593, granted Oct. 18, 1988 in the name of Mikio Yamashita et al and entitled, "Method And Apparatus For Discriminating Minute Particles".

The existing prior art flow cytometer machines have several shortcomings, due primarily to the large variance in the scatter and fluorescence signals that are to be measured. This variance results in voltage signals over many orders of magnitude, all of which must be processed in order to identify the particular cell types. For example, the voltage pulses obtained, after initially setting the machine, can vary from less than five millivolts to more than ten volts. State of the art analog electronic components cannot adequately handle voltage variations over this range in performing analog subtractive normalization techniques and log amplification. These analog electronic components are highly sensitive to thermal drift effects and have bandwidth limitations for pulse detection applications. Another problem with existing flow cytometer machines is that the time to process the signal information limits the rate at which cells can be detected. This latter problem, in turn, increases the time for performing a differential analysis of the cells in a given sample. A need exists to solve both of these problems.

SUMMARY OF THE INVENTION

In accordance with one aspect of the invention, there is provided a flow cytometer for detecting and identifying particles in a fluid. The flow cytometer has means for moving the particles to a detection station, means for directing energy at the detection station so that the particles intersect the energy when at the detection station, and a plurality of detectors for providing analog electric signals manifesting different results of each particle intersecting the energy. The flow cytometer includes a plurality of analog signal processors, each responsive to one detector signal for processing, delaying and storing analog data manifesting the signal provided thereto, and first controller means responsive to a trigger signal from a selected one of the analog signal processors for determining that a particle is intersecting the energy. The trigger signal is time related to the signals from the detectors and the first controller means provides signals to each of the analog signal processors for causing the storage of a delayed version of the signal applied thereto. Further, the flow cytometer includes second controller means for polling each of the plurality of analog signal processors to receive and digitize the delayed signal stored thereby and to further process the received and digitized signals in order to identify the detected particle.

In accordance with another aspect of the invention, there is provided a flow cytometer for detecting particles in a fluid and determining information regarding the particles. The flow cytometer has means for moving the particles to a detection station, means for directing energy at the detection station so that the particles intersect the energy when at the detection station, and detector means for providing an electric signal manifesting the result of each particle intersecting the energy. The flow cytometer further has a detection circuit including means for detecting the presence of a particle in the detection station, first storage means for storing an electric signal related to the detector means signal after the means for detecting has detected a particle in the detection station, and second storage means for storing, on command, an electric signal related to the signal stored by the first storage means. In addition, the detection circuit includes processor means responsive to the electric signal stored by the second storage means for processing the electric signal stored by the second storage means to obtain the information regarding each particle, and command means for enabling the second storage means to store the electric signal related to the signal stored by the first storage means after the processor means has completed processing the electric signal previously stored by the second storage means and the means for detecting has detected the presence of another particle in the detection station.

In accordance with still another aspect of the invention, there is provided apparatus for detecting particles. The apparatus has means for moving the particles to a detection station, means for directing energy at the detection station so that the particles intersect the energy when at the detection station and detector means for providing an analog electric signal manifesting a result of each particle intersecting the energy, the detector means signals varying in magnitude over a certain range. The particle detecting apparatus further has converter means for converting an analog electric signal applied to an input thereof to a digital signal, the convertor means having a certain number, n, of digital outputs for manifesting the digital value of the analog signal provided to the converter means input. The improvement includes first and second amplifiers, each responsive to the detector means signal, the first amplifier having a first gain and the second amplifier having a second gain, the second gain being greater than the first gain. The improvement further includes switch means having a pair of inputs, each connected to a different one of the first and second amplifiers, and an output switchably connected with one of the inputs in response to a switch signal provided to the switch means, a switch means output signal appearing at the output. Further, the improvement includes means for determining whether the second amplifier signal exceeds a certain value and for providing the switch signal to the switch means to connect the output with the first input whenever the second amplifier signal exceeds the certain value and to connect the output with the second input whenever the second amplifier signal does not exceed the certain value. The switch means output signal is coupled to the converter means input for conversion by the converter means to a digital signal manifested in n-m of the converter digital outputs, where m is at least one, the switch signal being contained in the remaining converter means digital outputs.

BRIEF DESCRIPTION OF THE DRAWINGS

One preferred embodiment of the subject invention is hereafter described with specific reference being made to the following Figures, in which:

FIG. 8 is a block diagram of the data acquisition logic shown in FIG. 2;

FIG. 9 is a block diagram of the CPU shown in FIG. 2; and

DETAILED DESCRIPTION

Figure 1:
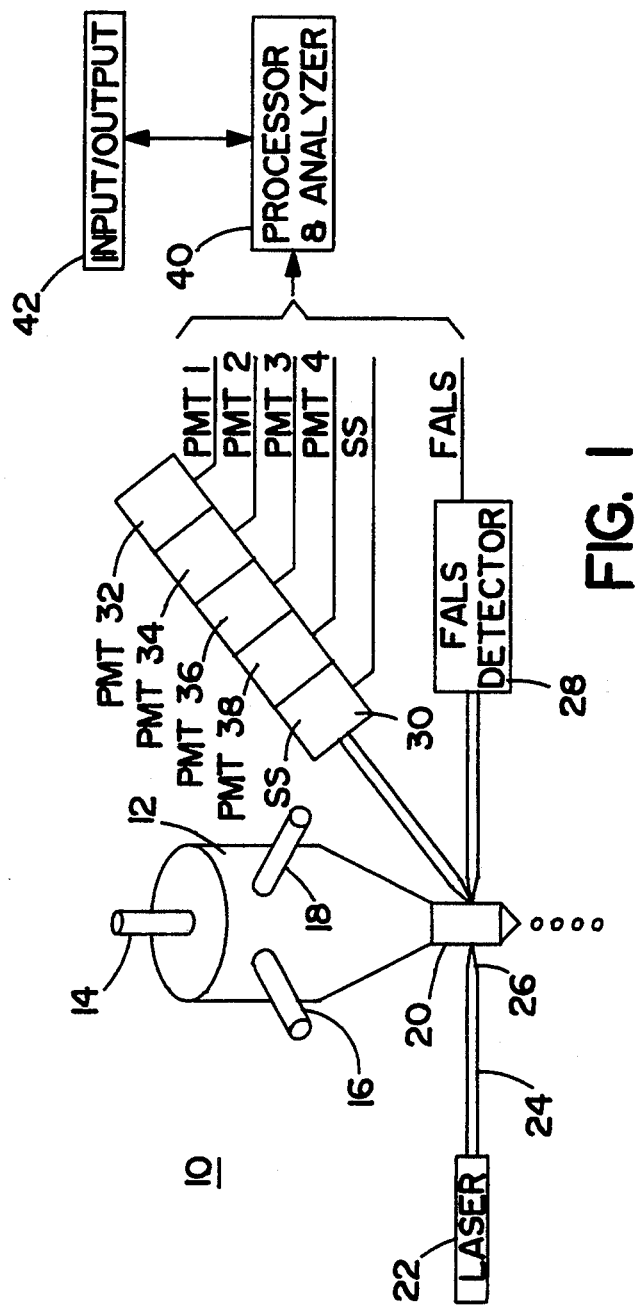
FIG. 1 is a diagram of the flow cytometer of the subject invention.

Referring now to FIG. 1, a schematic illustration of a flow cytometer 10 embodying the subject invention is shown. The key component of system 10 is a flow chamber 12, which includes a sample inlet 14 for receiving a sample containing particles, such as stained blood cells, to be identified, a waste outlet 16 and a sheath inlet 18 for receiving a sheath fluid. In addition, flow chamber 12 includes a detection station 20 through which the cells to be identified pass while contained in a narrow stream or column of sample fluid surrounded by the sheath fluid. A laser mechanism 22 directs a 488 nanometer laser beam 24 through focusing optics 26 towards detection station 20. Alternatively, beam 24 can be a combination of an argon laser beam and a dye laser beam or a helium-neon laser beam used specifically to excite molecules on the stained cells, thereby causing fluorescent light to be emitted.

Various different type of cells can be detected by measuring the light scattered from the cell, as well as the fluorescent energy generated by the energized dye. The light scatter is detected by a forward angle light scatter (FALS) photo-detector 28 and a ninety degree light scatter, or side scatter (SS), photo-detector 30. Forward angle light scatter photo-detector 28 is positioned in the path of laser beam 24 on the opposite side of detector station 20 and side scatter photo-detector 30 is positioned generally perpendicular to laser beam 24. Photo-detectors 28 and 30 measure the forward scattered light and side scattered light from the cell being detected as a result of the focusing of laser beam 24 on the cell. Each of photo-detectors 28 and 30 includes photodiodes for detecting light having the laser beam 24 wavelength of 488 nanometers.

The forward angle light scatter photo-detector 28 has two large area silicon planar diffused photodiodes. The side scatter photo-detector 30 has a single small area PIN photodiode. Because of the wide variation of light intensity in the forward direction, photo-detector 28 can include an operator insertable ND1 filter which, when inserted, reduces the intensity by a factor of ten. This filter should be used whenever large particles, that is particles larger than 20 microns in diameter, are being identified. Similarly, photo-detector 30 can include an operator changeable dichronic beam splitter to reduce the light intensity where large granular cells are being identified. As the light hits the photodiodes, electric current is generated (similar to a solar cell) and this current is then transformed to a voltage pulse by a preamp as the photo-detectors 28 and 30 data signals, FALS and SS. The FALS and SS signals, thus, manifest the amount of light scattered in the forward direction and the side direction whenever a cell is being identified in detector station 20.

The fluorescent emission from the detected cell, caused by beam 24 energizing the staining material on the cell, is measured by a plurality, such as four, of photomultiplier tubes (PMT's) 32, 34, 36 and 38, positioned 90 degrees with respect to the direction of laser beams 22 and 24. Each photomultiplier tube 32, 34, 36 and 38 provides a data signal manifesting the intensity of fluorescent light scatter at a particular frequency (color), and each photomultiplier tube 32, 34, 36 and 38 respectively provides a voltage, labeled PMT1, PMT2, PMT3 and PMT4, manifesting the intensity of the detected fluorescent light.

The six light sensors 28, 30, 32, 34, 36 and 38 are used to collect information regarding the size, granularity and uptake of the fluorescent markers of the cell being detected, and this information is, in turn, used to aid in identifying the particular type of cell. The various data signals FALS, SS, PMT1, PMT2, PMT3 and PMT4 from detectors 28, 30, 32, 34, 36 and 38 are applied to a processor and analyzer 40, which also receives signals from an input/output device 42, such as conventional computer keyboard, display and printer devices. The data signals FALS, SS, PMT1, PMT2, PMT3 and PMT4 are each analog voltages ranging in amplitude from less than one millivolt to more than ten volts. Among the signals provided from input/output device 42 to processor/analyzer 40 are various operator generated programming signals used to program processor/analyzer 40 regarding the type of cell to be identified or the type of stain placed on the cells. In addition, various other signals can be used to indicate that system 10 has been turned on or off. The signals provided from processor/analyzer 40 to input/output device 42 include the information regarding the detected cells.

Figure 2:
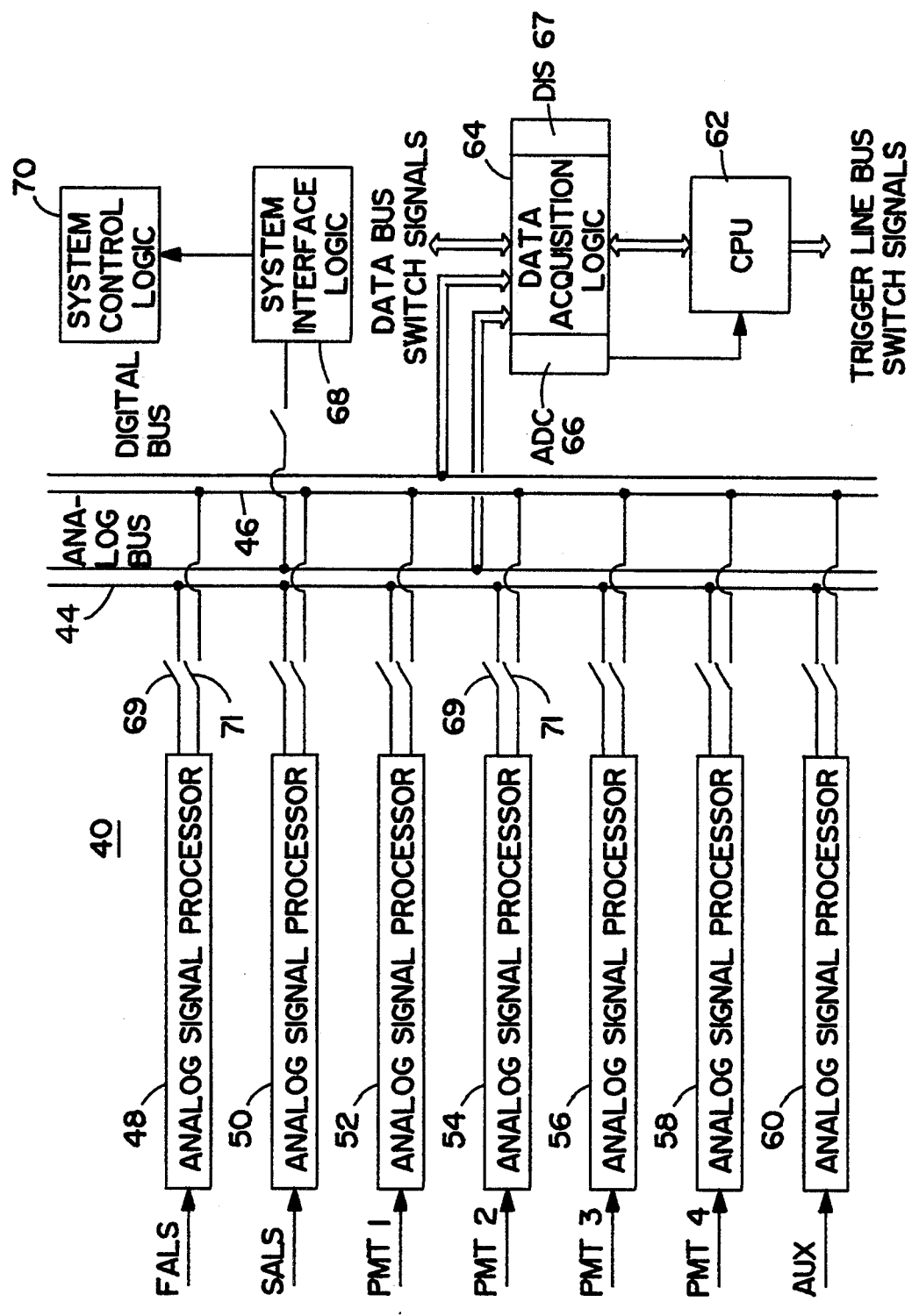
FIG. 2 is block diagram of the signal processing, digital conversion and identification circuits of the subject invention.

Referring now to FIG. 2, a block diagram of the signal processor/analyzer 40 is shown. Processor/analyzer 40 includes a pair of buses, a analog bus 44 and a digital bus 46, used to interconnect the various elements of processing/analyzer 40. Generally, analog bus 44 transmits various analog voltage signals and digital bus 46 transmits various digital controls signals and each bus includes several different lines. Processor/analyzer 40 also includes six identical principal analog signal processors 48, 50, 52, 54, 56 and 58 connected to each of buses 44 and 46. Each of the six principal analog signal processors 48, 50, 52, 54, 56 and 58 responds to one of the FALS, SS, PMT1, PMT2, PMT3 and PMT4 voltages from detectors 28, 30, 32, 34, 36 and 38 shown in FIG. 1.

A seventh analog signal processor 60 is also provided as either an auxiliary channel to receive data from one of the six principal analog signal processors 48, 50, 52, 54, 56 and 58 to measure an additional parameter of the cell being identified, or the seventh analog signal processor 60 can be used in conjunction with one of the six principal analog signal processors 48, 50, 52, 54, 56 and 58 to provide additional information about a single signal. For example, the principal analog signal processor 48, 50, 52, 54, 56 or 58 can detect the integral of the voltage and the seventh analog signal processor can 60 detect the peak voltage from the same light sensor 28, 30, 32, 34, 36 and 38. While the circuitry on each of the seven analog signal processors 48, 50, 52, 54, 56 and 60 is identical, some circuits are not used and these will be noted hereafter with respect to the description of the analog signal processor circuit shown in FIGS. 3, 4 and 5.

In addition, processor analyzer 40 includes a central processor unit (CPU) 62 and a data acquisition logic system 64, which includes an analog to digital convertor 66 for converting the analog data from the analog signal processors 48, 50, 52, 54, 56, 58 and 60 to digital data for provision to CPU 62 for further processing. In addition, data acquisition logic 64 includes a discriminator 67 used to determine when a cell is positioned for identification in detection station 20. Finally, processor analyzer 40 includes a system interface logic circuit 68 and system control logic circuit 70, which together control various other portions of system 10, such as laser 22, the fluid and pneumatic systems, and the like, which are beyond the scope of this invention, but necessary and well known in conventional flow cytometer machines.

Each of the analog signal processors 48, 50, 52, 54, 56, 58 and 60 are connected to provide analog pulse voltage signals to the analog bus 44 by the closure of a switch 69 and each of the analog signal processors 48, 50, 52, 54, 56, 58 and 60 are connected to receive digital control signals through digital bus 46 by the closure of a switch 71. The closure of switches 69 is generally controlled by CPU 62 and data acquisition logic 64 and the closure of switches 71 is generally controlled by CPU 62. With respect to analog bus 44, only one of the analog signal processors 48, 50, 52, 54, 56, 58 or 60 provides a signal to any bus line at any given time.

Normally, as a cell becomes positioned in detection station 20 and intersects laser beam 24, the various light detectors 28, 30, 32, 34, 36 and 38 provide a Gaussian pulse output voltage signal. Voltage discriminator 67 which is included within data acquisition logic 64, detects when the voltage level is above a certain minimum, as an indication that a cell is about to be positioned for identification. The cell position information is provided from a pre-selected one of the analog signal processors 48, 50, 52, 54, 56 or 58 to the discriminator 67 over one line of analog bus 44. After discriminator 67 detects that a cell is about to be positioned for identification, data acquisition logic 64 provides controls signals to the analog signal processors 48, 50, 52, 54, 56, 58 and 60 to accept the voltage data from the corresponding light detectors 28, 30, 32, 34, 36 and 38 and store either the time domain integral value, or the peak voltage value, of the provided pulse voltage in a sample and hold circuit. Thereafter, the stored analog voltage from one analog signal processor 48, 50, 52, 54, 56, 58 and 60 at a time is provided to the data acquisition logic 64, passed through the analog to digital convertor 66 and to CPU 62, for further processing and cell identification.

As will be described in more detail hereafter, because the rate that cells enter detection station 20 is random, and the time to process the data is finite, situations will arise when a new cell is positioned for detection before the entire data from the proceeding cell is fully analyzed. To accommodate this situation, each analog signal processor 48, 50, 52, 54, 56, 58 and 60 includes a pair of sample and hold circuits arranged so that new data can be accepted while the old data is awaiting transmission to data acquisition logic 64. Further, CPU 62 is arranged in a pipeline arrangement so that it can be processing data from multiple detections at the same time.

Figure 3:
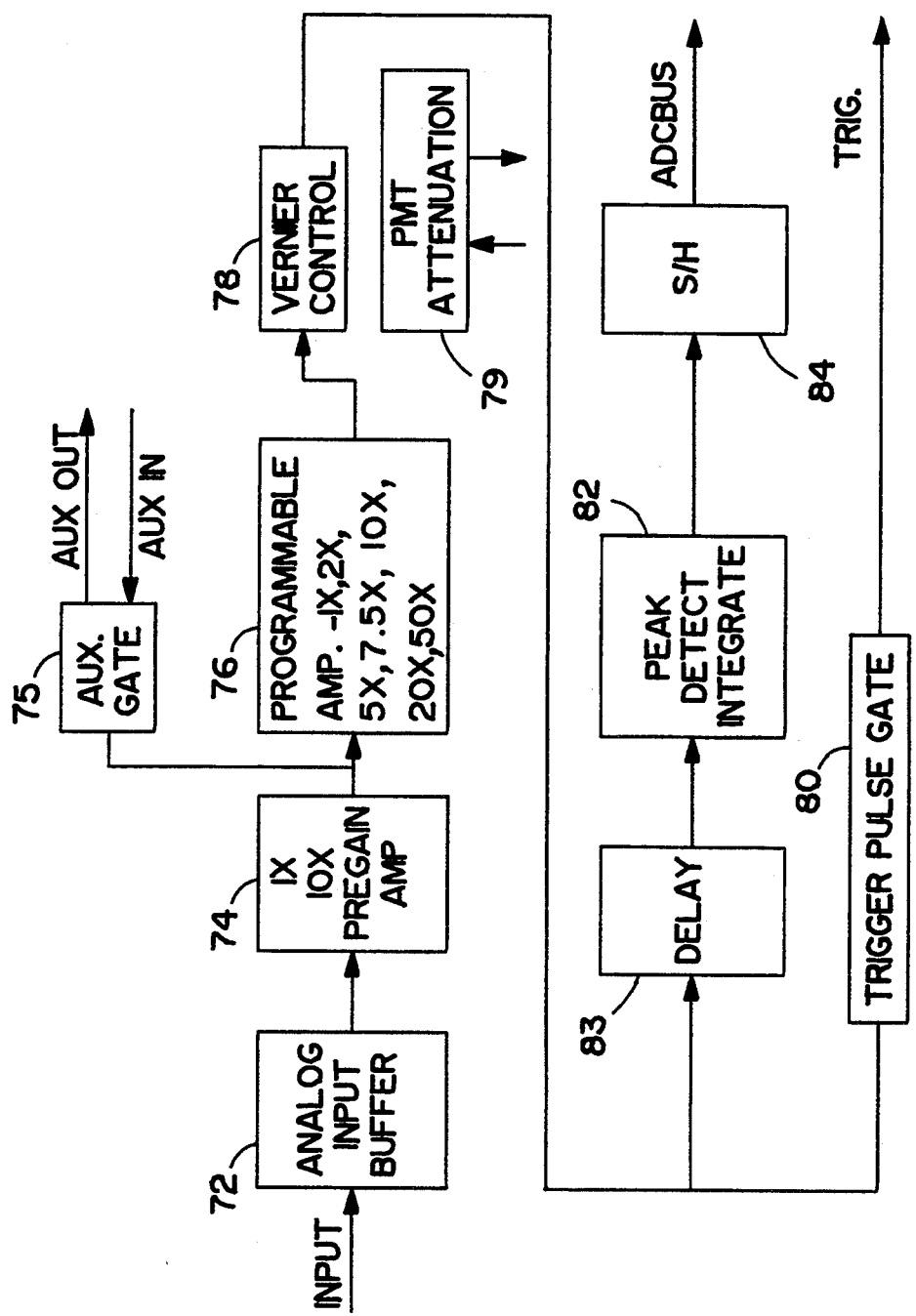
FIG. 3 is a diagram showing the functions of the analog signal processor shown in FIG. 2.
Figure 4:
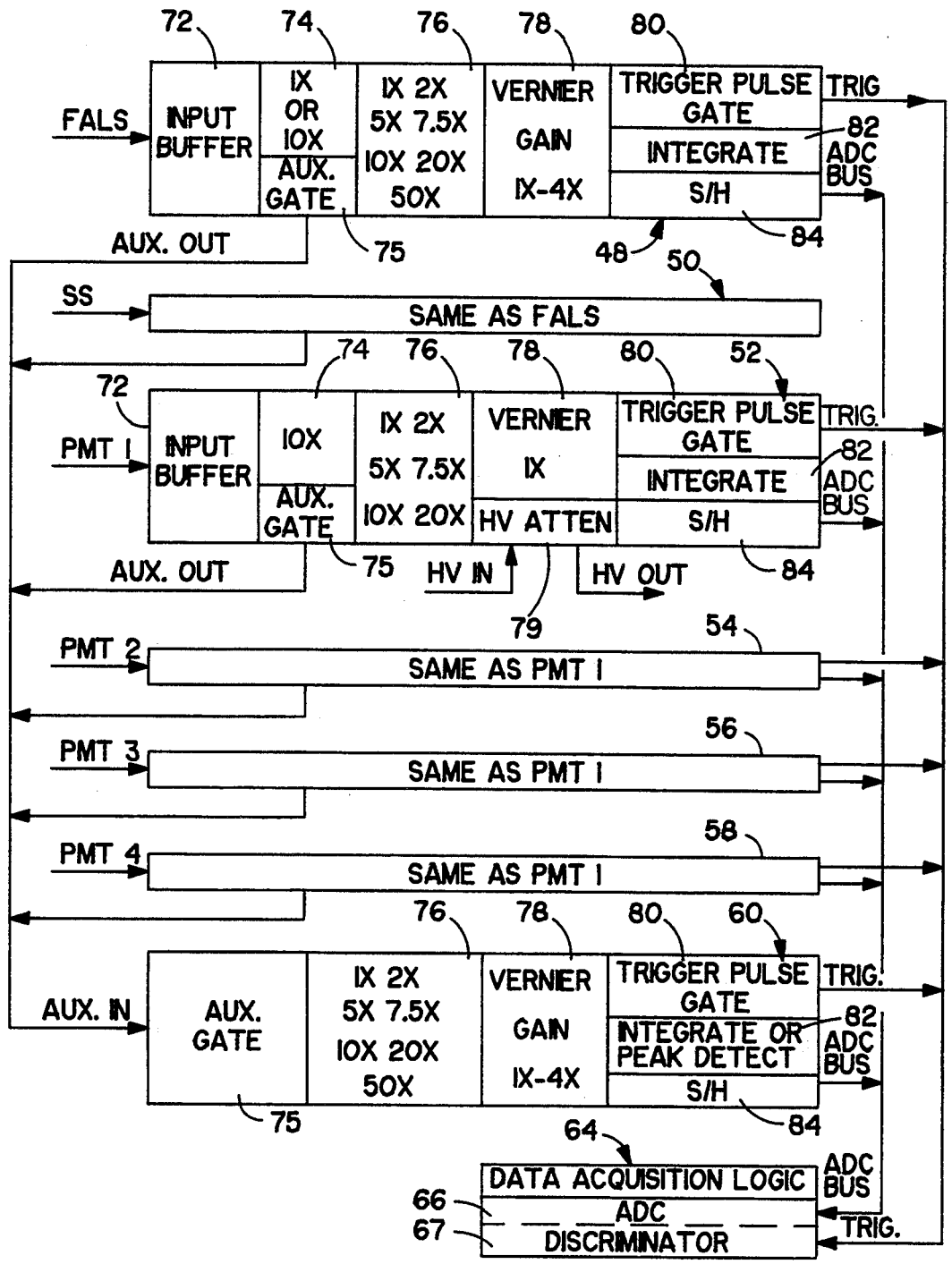
FIG. 4 shows the manner in which the various analog signal processors are interconnected for the various signals detected by the flow cytometer shown in FIG. 1.

As noted above, each of the analog signal processors 48, 50, 52, 54, 56, 58 and 60 are constructed identically in order to obtain the efficiencies of mass production, but some circuits of each are bypassed for certain functions and others are programmed differently. FIG. 3 shows a functional generic depiction of one of the analog signal processors 48, 50, 52, 54, 56, 58 and 60 and FIG. 4 shows the manner in which the various functional aspects are used, as well as the manner in which the seven analog signal processors 48, 50, 52, 54, 56, 58 and 60 are interconnected.

Referring first to FIG. 3, each of the analog signal processors 48, 50, 52, 54, 56, 58 and 60 includes an analog input buffer section 72, which responds to an INPUT signal from an associated detector 28, 30, 32, 34, 36 and 38. The signal from buffer section 72 is provided to a linear pre-gain amplification section 74, having an amplifier with a selectable gain of either one or ten, and accordingly is labeled as 1×/10×. The output from pre-gain amplification section 74 is provided to programmable gain section 76, which is programmable by the operator to have a gain of either one, two, five, seven and a half, ten, twenty or fifty. The line connecting sections 74 and 76 is switchably connected by AUX gate 75 to the AUX line of analog bus 44, so that the output from pre-gain amplification section 74 of principal analog signal processors 48, 50, 52, 54, 56 and 58 can be provided to the AUX bus line and the signal on the AUX bus line can be provided to programmable gain section 76 of the auxiliary analog processor 60.

The output from programmable gain section 76 is coupled to vernier control section 78, which is used to fine tune the gain of the FALS, SS and AUX signals in analog signal processors 48, 50 and 60. A separate attenuator section 79 is used for analog signal processors 52, 54, 56 and 58, which respond to the signals from the PMT detectors 32, 34, 36 and 38. The output from vernier control section 78 is provided through trigger pulse gate 80 as the TRIG signal provided over analog bus 44 to discriminator 67 and used by discriminator 67 to detect whether a cell is about to be positioned in detection station 20.

The output from vernier control section 78 is also delayed by delay 83 and provided to one of a peak detector or an integrator in section 82. The output analog voltage from section 82 is then stored in a sample and hold section 84 for subsequent provision over the ADCBUS line of analog bus 44 to analog to digital converter 66 in data acquisition logic 64.

FIG. 4 shows the manner of interconnecting and enabling the various parts of the six principal analog signal processors 48, 50, 52, 54, 56 and 58 for each of the various detected light signals FALS, SS, PMT1, PMT2, PMT3 and PMT4 applied thereto, as well as for the auxiliary analog signal processor 60. For the analog signal processors 48 and 50, receiving the FALS and SS signals, the processor programmable gain of pre-gain amplifier 74 is either one or ten. Generally, the gain is selected to be one, but can be set to ten where small particles are being detected. On the other hand for the analog signal processors 52, 54, 56 and 58 receiving the PMT1, PMT2, PMT3 and PMT4 signals, pre-gain amplifier 74 is always set with a fixed gain of ten because the fluorescent light intensity is normally lower than the forward scatter light. For the auxiliary analog signal processor 60, the input signal completely bypasses both input buffer 72 and pre-gain amplifier 74.

Each of the seven analog signal processors 48, 50, 52, 54, 56, 58 and 60 use the variable gain amplifier; however, the gain of fifty setting is only programmed in analog signal amplifiers 48, 50 and 60 receiving the FALS, SS and AUX signals. Each of the analog signal processor 48, 50, 52, 54, 56, 58 and 60 use the integrator in section 82 and the sample and hold section 84. In sum circumstances, auxiliary analog signal processor 60 will use the peak detector in place of the integrator.

As seen in FIG. 4, the output from each of the 1×/10× amplifier stage section 74 in analog signal processors 48, 50, 52, 54, 56 and 58 is capable of being provided through AUX gate 75 as the AUXOUT signal, which is provided to auxiliary analog signal processor 60 as the input signal, AUXIN, thereof. The particular one of the signals to be applied to auxiliary analog signal processor 60 is selectable by commands from CPU 62 enabling only one of the AUX gates 75. In addition, the sample and hold output of each analog signal processors 48, 50, 52, 54, 56 and 60 is applied as the ADCBUS signal to analog to digital convertor 66, which is a part of data acquisition logic 64. Further, the trigger pulse gate 80 from only one of the analog signal processors 48, 50, 52, 54, 56 and 60 will be enabled to apply the TRIG pulse signal to discriminator 67, which is also a part of the data acquisition logic 64.

Figure 5:
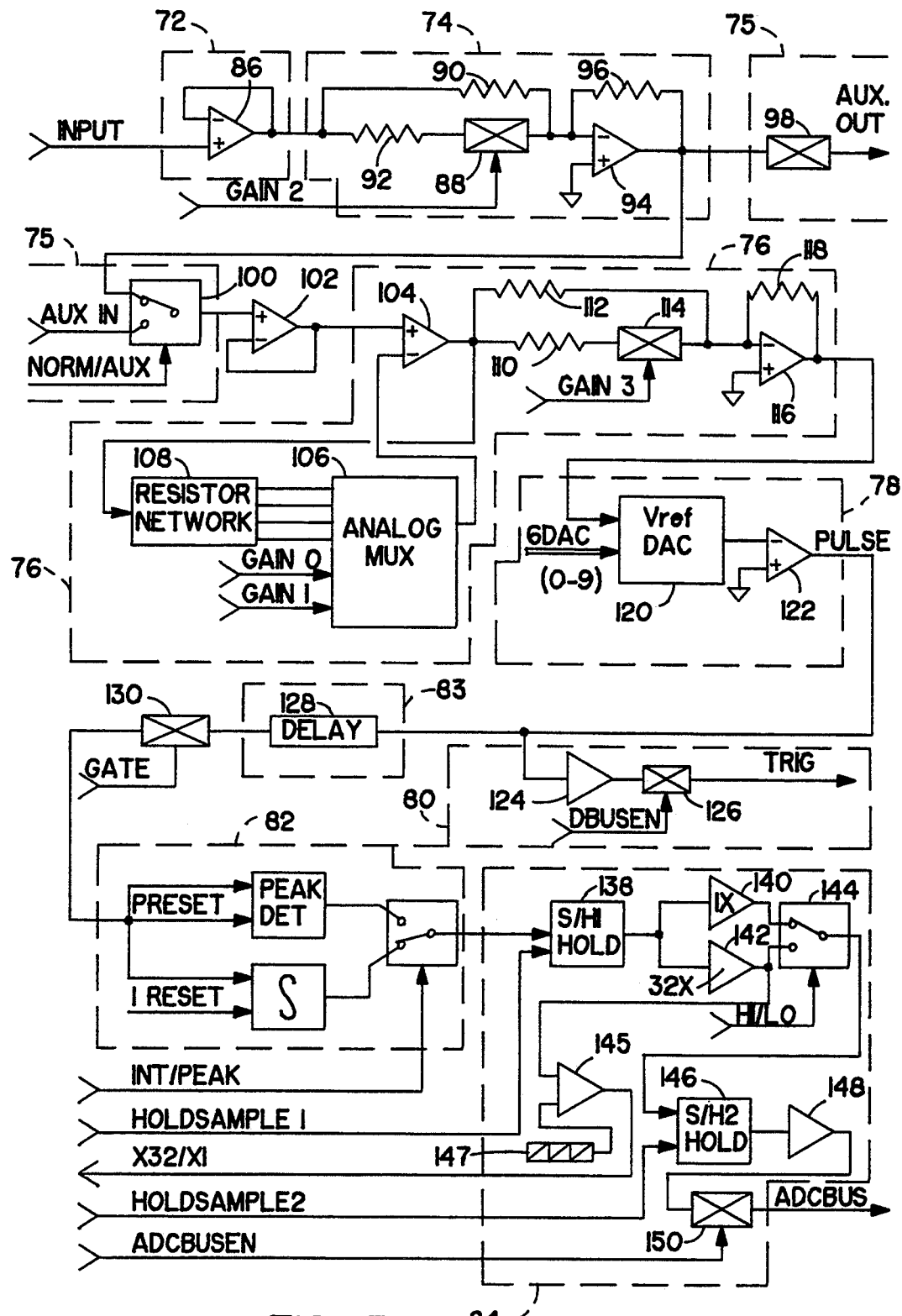
FIG. 5 is a block diagram of one of the analog signal processors.

Referring now to FIG. 5, a more detailed block diagram of any one analog signal processors 48, 50, 52, 54, 56, 58 or 60, is shown. The input signal, designated INPUT in FIG. 5, can be any one of the FALS, SS, PMT1, PMT2, PMT3 and PMT4 signals previously discussed. As will be explained hereafter, various parts of the generic analog signal processor circuit are enabled or disabled depending upon the type and/or magnitude of the INPUT signal.

The INPUT signal is first passed through a non-inverting buffer amplifier 86, which represents the input buffer section 72 shown in FIGS. 3 and 4, and which can include multiple stages and various well known signal conditioning circuits. The output of buffer amplifier 86 is coupled to the 1×/10× amplifier section 74; specifically the output of amplifier 86 is coupled to one end of a serially coupled resistor 92 and switch 88. A second resistor 90 is coupled in parallel with serially coupled resistor 92 and switch 88. Switch 88 is opened or closed in response to a GAIN2 signal provided over digital bus 46 from CPU 62. As will be explained in more detail with respect to FIG. 7, a data bus and an address bus from CPU 62 is provided as a part of digital bus 46 and various control signals, such as a series of switch signals discussed herein and labeled GAIN0 through GAIN3, are provided by various addressable registers.

The other ends of resistor 90 and switch 88 are coupled together and to the inverting input of operational amplifier 94; further, a resistor 96 is coupled between the output and input of amplifier 94. The values of resistors 90 and 96 are selected to be the same and the value of resistor 92 is selected so that the parallel combination of resistor 90 and 92 is approximately ten percent of the value of resistor 96. Thus, when switch 88 is closed, the output of amplifier 94 is a voltage ten times the buffered INPUT signal voltage and when switch 88 is open, the output of amplifier 94 is a voltage equal to the buffered INPUT signal voltage.

The output of amplifier 94 is connected to the input of analog switch 98, which is controlled by the magnitude of the AUXOUTEN signal to permit the output of amplifier 94 to be provided as the AUXOUT signal to the auxiliary analog signal processor 60 over an AUX bus line in analog bus 44. Switch 98 can be closed when it is desired to use the auxiliary analog signal processor 60 to detect another parameter, such as the peak value, for one of the INPUT signals, or when it is desirable to use the auxiliary analog signal processor 60 for a linear integral function while the six principal analog signal processors 48, 50, 52, 54, 56 and 58 have their gains set at one for logarithmic applications.

The output of amplifier 94 is also connected to one input terminal of an analog switch 100; the other input terminal of switch 100 has the AUXIN signal connected thereto, which normally is a selected one of the AUX-OUT signals. The position of the switch arm of switch 100 is controlled by the NORM/AUX control signal, which is provided over digital bus 46 from CPU 62. Normally, for the principal analog signal processors 48, 50, 52, 54, 56 and 58, the NORM/AUX signal connects the output of amplifier 94 through switch 100 and for the auxiliary analog signal processor 60, the NORM/AUX signal connects the AUXIN signal through switch 100. The two switches 98 and 100 constitute the AUX gate shown in FIGS. 3 and 4.

The signal at the output terminal of switch 100 is amplified by buffer amplifier 102 in order to remove switch losses and provided to variable gain amplification section 76 at the non-inverting input of operational amplifier 104. The inverting input to amplifier 104 is coupled to the output of analog multiplexer (MUX) 106. Analog multiplexer 106 has four inputs coupled to resistor network 108. Amplifier 104, multiplexer 106 and resistor network 108 are configured as a closed loop programmable gain amplifier, with programmable gains of one, two, five and seven and one half. Two address signals, labeled GAIN0 and GAIN1, generated by CPU 62 and provided over digital bus 46, are used to select which of the four lines are coupled by analog multiplexer 106 to the inverting input of amplifier 104, thereby permitting the gain of amplifier 104 to be selected as either one, two, five or seven or one half.

The output of amplifier 104 is coupled to one end of each of resistors 110 and 112. The other end of resistor 110 is coupled through analog switch 114, which is opened or closed in response to the GAIN3 signal, and the output terminal of switch 114 is coupled to the other end of resistor 112 and to the inverting input of operational amplifier 116. The non-inverting input of amplifier 116 is grounded and the output of amplifier is coupled through resistor 118 to the inverting input thereof. The value of resistors 112 and 118 are the same and the value of resistor 110 is selected to be such that when resistor 110 is in parallel with resistor 112, the combination is approximately ten percent of the value of the value of resistor 118. Accordingly, the circuit consisting of switch 114, resistors 110, 112 and 118 and amplifier 116 is selectable to amplify with a gain of either one or ten. It should be noted that the combination of the amplifier 104, multiplexer 106 resistor network 108 and the amplifier 116 circuit permits the gain of amplification section 76 to be selected to be one, two, five, seven and a half, ten, twenty, fifty or seventy-five, the latter of which is not currently used in any of the analog signal processors 48, 50, 52, 54, 56, 58 and 60.

The output from variable amplification section 76, at the output of amplifier 116, is provided to attenuation section 78, which includes digital to analog convertor (DAC) 120 and operational amplifier 122. The output from amplifier 116 is provided to the reference voltage (Vref) input of digital to analog convertor 120 and a ten bit digital signal, labeled GDAC, having a digital value between 1024 and 4095, is provided to the digital inputs of digital to analog convertor 120. The GDAC signal is provided from CPU 62 over digital bus 46 and latched within the addressed analog signal processor 48, 50, 52, 54, 56, 58 or 60, as will explained hereafter with respect to FIG. 7. The output of digital to analog convertor 120 is then an analog signal corresponding to a scaled version of the input analog signal from amplifier 116, the scaling being between twenty-five percent and one hundred percent in tenth of a percent increments, and the particular scaling factor is determined by the digital value of the GDAC signal.

Figure 6:
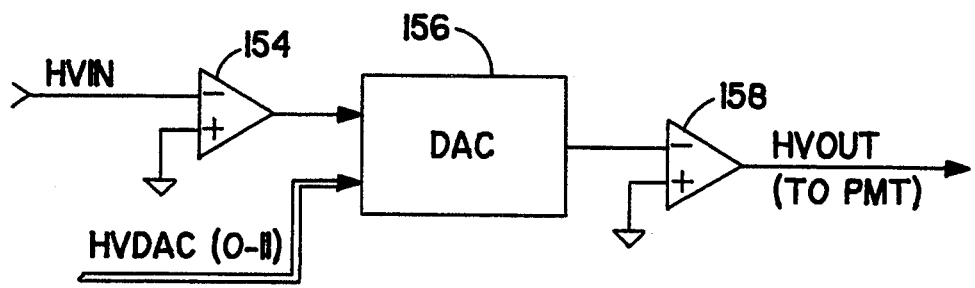
FIG. 6 is a block diagram of the PMT high voltage scaler circuit.

The output from digital to analog convertor 120 is provided to the inverting input of operational amplifier 122 which amplifies the analog signal with a gain of four. Thus, the total amplification in section 76 is between one and four in increments of 0.001. It should be noted that for the PMT signal analog signal processors 52, 54, 56 and 56, the value of the GDAC signal is always 1024, so the vernier fine control scaling function just described is not available for those analog signal processors 52, 54, 56 and 56. Rather, a separate vernier circuit 79, shown in FIG. 6, is used for the fine control function.

The output from amplifier 122 is labeled as the PULSE signal and is an analog signal, properly amplified and scaled, representing the signal data from one of the light sensors 28, 30, 32, 34, 36 and 38 used to sense light intensity information regarding the cell being identified. The PULSE signal is a pulse which begins increasing in value as a cell enters the detection station 20 and returns to zero as the cell leaves detection station 20. The cell is positioned for identification when the value of the PULSE signal is above a certain threshold voltage.

In order to first determine the presence of a cell in detection station 20, the PULSE signal is provided from trigger pulse gate 80 of one selected analog signal processors 48, 50, 52, 54, 56, 58 or 60. In order to monitor the PULSE signal, it is provided through an output driver amplifier 124 and an analog switch 126 to analog bus 44, and is labeled as the TRIG signal. Switch 126 is enabled by a control signal DBUSEN, provided from CPU 62 over digital bus 46 and decoded within the selected and addressed analog signal processor 48, 50, 52, 54, 56, 58 or 60, as previously explained. As noted above, only one of the analog signal processors 48, 50, 52, 54, 56, 58 or 60 is selected to provide the TRIG signal to CPU 62 and that one analog signal processors 48, 50, 52, 54, 56, 58 or 60, together with discriminator 67 in data acquisition logic 64, will function as the system discriminator for identifying that a cell is about to be positioned for detection and data analysis. Normally analog signal processors 48 responding to the FALS signal is selected to provide the TRIG pulse signal as the input to discriminator 67 because normally all events scatter light in the forward direction.

In order to permit the entire PULSE signal to be analyzed after it is detected as a real signal by the trigger pulse gate 80 and discriminator 67, it is provided through a five microsecond delay circuit 128 and re-labeled as the DPULSE signal. During the five microsecond delay, the TRIG signal is monitored and after it is detected as manifesting a cell about to be positioned for detection and identification, the data acquisition logic 64 controls the peak and integral capture functions on analog signal processors 48, 50, 52, 54, 56, 58 and 60, all simultaneously. Thereafter, the captured value is held for further processing, as will be explained in more detail hereafter with respect to FIG. 8.

The DPULSE from delay circuit 128 is provided through analog switch 130 to peak detector/integrator section 82, which includes a peak detector circuit 132 and an integrator circuit 134. Switch 130 is opened or closed in response to a GATE signal, provided to each analog signal processors 48, 50, 52, 54, 56, 58 and 60 in response to control signals from the data acquisition logic 64 after the TRIG signal has been found to represent a cell about to be positioned for detection. Peak detector circuit 132 is a conventional electronic circuit which stores the maximum value of the voltage provided thereto and integrator circuit 134 is a conventional integrator circuit which provides a voltage manifesting the real time integral of the voltage signal applied thereto. Both peak detector circuit 132 and integrator circuit 134 include capacitors (not shown) which store the peak or integral voltage values and which are reset by application thereto of the respective PRESET and IRESET signals.

The outputs of integrator circuit 134 and a peak detector circuit 132 are coupled to a different one of the two inputs of analog switch 136. The particular input signal to switch 136 provided to the output thereof is controlled by the state of control signal INT/PEAK provided from CPU 62 over digital bus 46. The signals from peak detector circuit 132 and integrator circuit 134 both are useful in identifying various types of blood cells and either type can be selected for the various ones of the FALS, SS, PMT1, PMT2, PMT3 and PMT4 signals provided to analog signal processors 48, 50, 52, 54, 56, 58 and 60. Generally, however, integrator circuit 134 is selected for the six principal analog signal processors 48, 50, 52, 54, 56 and 58 and peak detector 132 is selected in the auxiliary analog signal processor 60.

The output signal from switch 136 is coupled to a first sample and hold circuit 138, which stores the value of the signal provided thereto when placed in the hold mode. The output from the first sample and hold circuit 138 is coupled to both a first amplifier 140 set to have a gain of one and second amplifier 142 set to have a gain of thirty-two. The outputs of the two amplifiers 140 and 142 are coupled to the two inputs of analog switch 144. The purpose of providing the two amplifiers 140 and 142 having different gains is to permit analog to digital convertor 66 to operate over a greater range of analog voltages with an acceptable resolution. This is discussed hereafter in more detail with respect to FIG. 7.

The output of amplifier 142 is also connected as one input of comparator 145, the other input of which has coupled thereto the output of a sawtooth pulse generator 147. The sawtooth signal provided by sawtooth generator can vary between approximately four and nine volts with a frequency of, for example, 150 hertz. The output of comparator 145 is a digital signal, labeled X32/X1, and indicates whether or not the voltage at the output of amplifier 132 exceeds the voltage at the output of sawtooth generator 147.

Figure 7:
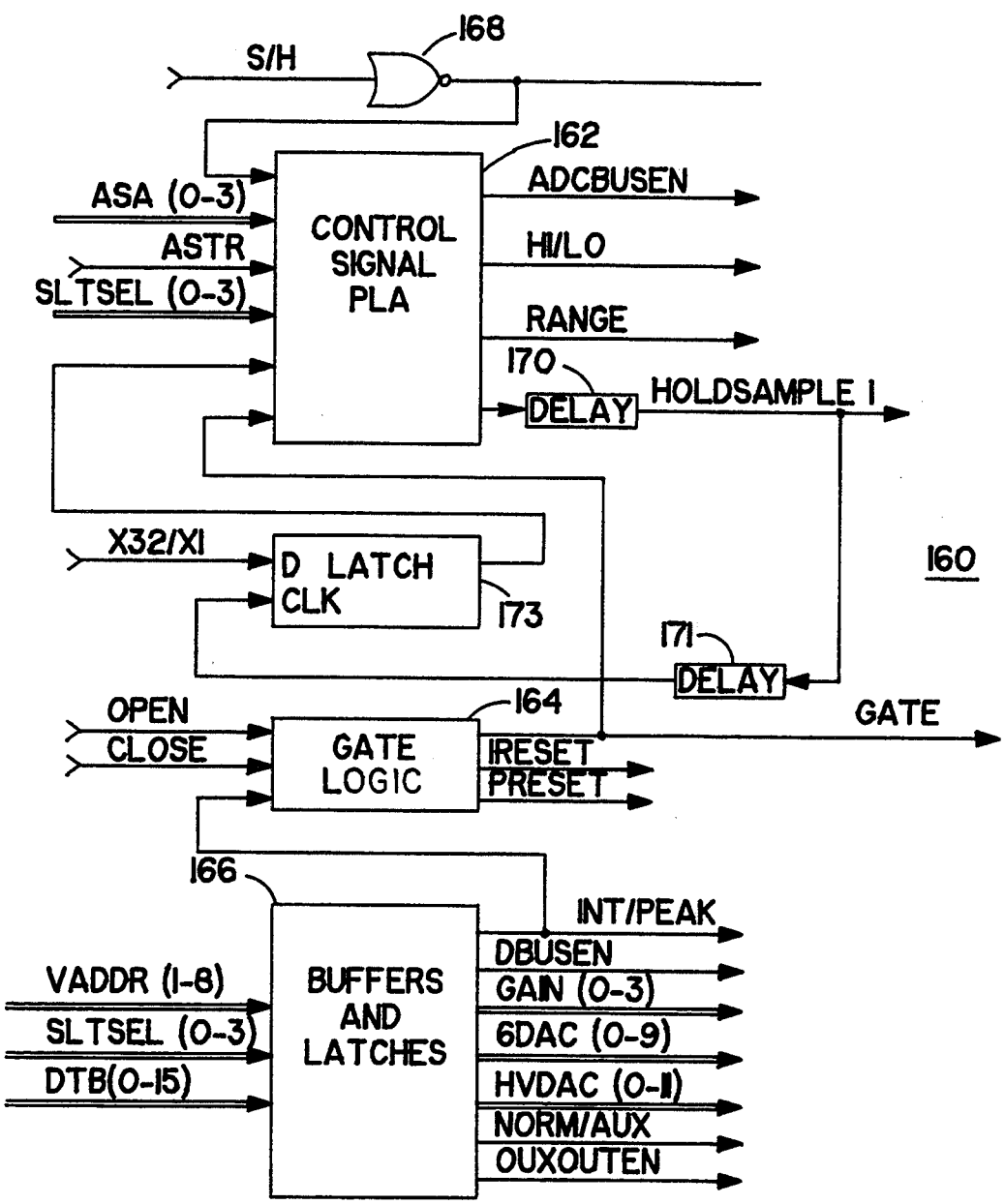
FIG. 7 is a block diagram of various control signal generating circuits used to provide the control signals for the analog signal processors.

The particular input signal to switch 144 selected to be provided to the output thereof is controlled by the state of control signal HI/LO provided from the control logic shown in FIG. 7. Whenever comparator 145 finds that the voltage at the output of amplifier 142 exceeds the instantaneous value of the sawtooth signal voltage, then it is desired to provide the amplifier 140 signal at the output of switch 144. On the other hand, whenever comparator 145 finds that the voltage at the output of amplifier 142 is less the instantaneous value of the sawtooth signal voltage, then it is desired to provide the amplifier 140 signal at the output of switch 144. As noted above and explained in more detail hereafter, the purpose of having the two amplifiers 140 and 142 and switch 144 is to extend the range of analog to digital converter 66 from sixteen bits to twenty bits. Because the results from operating flow cytometer 10 are displayed as a histogram, the presence of sawtooth generator 147 prevents a spike or gap from appearing on the histogram, which otherwise could occur had the crossover point been constant.

The signal at the output of switch 144 is then provided to a second sample and hold circuit 146, which, when placed in the hold mode, stores the value of the signal provided from the output of switch 144. The output of sample and hold circuit 146 is provided through amplifier 148 and analog switch 150 when the ADCBUSEN signal is provided from data acquisition logic 64. Thereafter, the output of sample and hold circuit 146 is provided over analog bus 44 to data acquisition logic 64 as the ADCBUS signal for further processing, as described hereafter.

Both the first and second sample and hold circuits 138 and 146 are enabled to store (hold) data provided thereto only during selected times by the respective HOLDSAMPLE1 and HOLDSAMPLE2 signals. The HOLDSAMPLE1 signal is provided from the logic shown in FIG. 7 in response to signals from data acquisition logic 64. The HOLDSAMPLE1 signal is maintained in at the sample mode state during the time integrator 134 or peak detector 132 are capturing data during the existence of the DPULSE pulse. A short time after the end of the DPULSE pulse, or event window, HOLDSAMPLE1 is switched to the hold mode state and the data captured by either integrator 134 or peak detector 132 is then held by first sample and hold circuit 138. The transfer of the data to second sample and hold circuit 146 from first sample and hold circuit 138 occurs when the HOLDSAMPLE2 signal is initiated by data acquisition logic 64. The HOLDSAMPLE2 signal is a pulse, initiated prior to the time analog to digital converter 66 is ready to accept data for digitalization from the various analog signal processors 48, 50, 52, 54, 56, 58 and 60.

The purpose of having the two sample and hold circuits 138 and 146 is to permit data from a new cell to be accepted prior to the point in time at which the data from the prior cell is fully analyzed. In other words, where two cells pass through detection station 20 closely spaced in time, the data (an analog voltage value) obtained from the first cell is transferred to sample and hold circuit 146 and the data from the second cell is captured in sample and hold circuit 138 while sample and hold circuit 146 is unavailable. When analog to digital convertor 66 is free from converting the prior cell data, it will cause the HOLDSAMPLE2 signal to be provided, thereby transferring the data from sample and hold circuit 138 to sample and hold circuit 146. The two sample and hold circuits 138 and 146 also eliminate problems due to a voltage loss by integrator 134 or peak detector if a long wait occurs before the data can be sent to sample and hold circuit 146 for transmission to data acquisition logic 64. At the time data acquisition logic 64 and CPU 62 are not busy processing data from the seven sample and hold circuits 146 from analog signal processors 48, 50, 52, 54, 56, 58 and 60, the HOLDSAMPLE2 signal is generated if data is present in sample and hold circuit 138, thereby causing that data to be transferred to sample and hold circuit 146 and freeing sample and hold circuit 138 to accept data from the next cell.

Referring now to FIG. 6, PMT vernier attenuation circuit 79 is shown. While circuit 79 is physically on the circuit board containing the analog signal processors 48, 50, 52, 54, 56, 58 and 60., it is independent of the circuit shown in FIG. 5. Circuit 79 is similar to the attenuation section 78 and is used to scale the high voltage applied to the PMT detectors 32, 34, 36 and 38. In circuit 79, the high voltage signal, HVIN, is provided through buffer amplifier 154 to the reference voltage input of a digital to analog convertor (DAC) 156. The digital inputs to digital to analog convertor 156 are coupled to the HVDAC 0–11 lines from CPU 62 and are set to scale the HVIN voltage as required. The output of digital to analog convertor 156 is provided through amplifier as the HVOUT signal to the PMT detectors 32, 34, 36 and 38.

Referring now to FIG. 7, there is shown a block diagram of the control signal interface circuit 160 used to provide the control signals discussed above in the analog signal processors 48, 50, 52, 54, 56, 58 and 60. Generally, various digital control signals are provided to interface 160 over digital bus 46 from either data acquisition logic 64 or CPU 62 to control the timing of the operation of the various switches and other elements in analog signal processors 48, 50, 52, 54, 56, 58 and 60. The primary components of interface 160 are a control signal programmable logic array (PLA) 162, gate logic 164 and a series of buffers and data latches 166.

PLA 162 has the HOLDSAMPLE2, ASA (0–3), ASTR, and SLTSEL (0–3) signals applied thereto, along with the GATE signal from gate logic 164. The HOLDSAMPLE2 signal, which enables sample and hold circuit 146, is obtained by inverting the S/H signal using inverter 168; the S/H signal, in turn, is issued by data acquisition logic 64 upon receipt of an acceptable TRIG signal from the selected trigger pulse gate 80 at a time after the integration or peak detection function has been completed. The ASA (0–3) signal is a four bit address signal and the ASTR signal is an address strobe signal, both of which are issued by data acquisition logic 64 to address the particular one of the analog signal processors 48, 50, 52, 54, 56, 58 or 60 to which the certain addressed control signal is applied. The SLTSEL (0–3) signal is a four bit code which is uniquely hard wired for each analog signal processors 48, 50, 52, 54, 56, 58 and 60 and against which the ASA (0–3) signal is compared for addressing purposes.

One output from PLA 162 is the HOLDSAMPLE1 signal, which is provided to enable sample and hold circuit 138 in response to the GATE signal from gate logic 164, and particularly the CLOSE signal portion thereof, and is delayed slightly by delay circuit 170. In addition, PLA 162 provides the ADCBUSEN and HI/LO signals. The ADCBUSEN signal enables gate 150 for the addressed analog signal processor 48, 50, 52, 54, 56, 58 or 60, so that the poled ADCBUS signal is provided over the ADCBUS line portion of analog bus 44.

The HOLDSAMPLE1 signal is further delayed by delay 171 and provided to the clock input of latch 173. The X32/X1 signal from comparator 145 is provided to the data input of latch 173 and the output of latch 173, which is provided as one of the inputs to PLA 162, then manifests whether the output from unity gain amplifier 140 or the thirty-two gain amplifier 142 is desired to be the signal to be stored in second sample and hold circuit 146. At the proper time, as determined by the GATE signal, the HI/LO signal is provided by PLA 162 to switch 144 to select the appropriate amplifier 140 or 142 output to be stored in sample and hold circuit 146. In addition, the RANGE signal is provided to data acquisition logic 64 to indicate the selected range to be used in further processing the data stored in sample and hold circuit 146. The RANGE signal correlates with the HI/LO signal.

Gate logic 164 has provided thereto the OPEN and CLOSE signals from data acquisition logic 64 and the INT/PEAK signal from buffers and latches circuit 166. The OPEN and CLOSE signals are used to generate the GATE signal permitting the output of delay 128 to be further processed and further determining the provision of the HI/LO signal generated by PLA 162. In addition, the OPEN and INT/PEAK signals are used to provide the PRESET and IRESET signals used to reset the storage capacitors in integrator 134 and peak detect circuit 132.

Buffers and latches circuit 166 is a conventional set of buffers and latches. A sixteen bit data signal DTB (0–15) is provided to a series of registers in circuit 166 and an eight bit address signal VADDR (1–8) is provided to a decoder circuit in circuit 166 from CPU 62. In addition, the SLTSEL (0–3) signal is connected to enable the decoder circuit. The decoder enables various ones of the registers to permit the output signals to be generated. The output signals provided by circuit 166 are the DBUSEN signal used to enable gate 126 and permit the initial system discriminator pulse to be provided to data acquisition logic 64; the GAIN1, GAIN2, GAIN3 and GAIN4 signals (labeled as the GAIN (0–3) signal) for controlling the gain of amplifier sections 74 and 76; the GDAC (0–9) and HVDAC (0–11) signals provided to digital to analog convertors 120 and 156; the INT/PEAK signal provided to gate 136 and gate logic 164; the NORM/AUX signal provided to gate 100; and the AUXOUTEN signal provided to gate 98. Each of these signals has been previously described.

Referring now to FIG. 8, a block diagram of data acquisition logic 64 is shown. Data acquisition logic 64 receives the addressed TRIG and ADCBUS analog signals from analog signal processors 48, 50, 52, 54, 56, 58 and 60 and provides a digital conversion of the ADCBUS signal to CPU 62. In addition, data acquisition logic 64 provides the various control signals to the analog signal processors 48, 50, 52, 54, 56, 58 and 60 and CPU 62. The TRIG signal from the selected one of the analog signal processors 48, 50, 52, 54, 56, 58 or 60 is provided as one input to an analog comparator circuit 174. The other input to comparator 174 has the output of a digital to analog convertor (DAC) 176 provided thereto. The input to digital to analog convertor 176 is a digital signal from CPU 62 provided over a sixteen bit data bus, DTB (0–15), interconnecting CPU 62 and data acquisition logic 64; for digital to analog convertor 176, only bits 0–9 of the data bus are used.

The output of comparator 174 changes states whenever the value of the TRIG signal exceeds the value of the output from digital to analog convertor 176. The signal from the output of comparator 174 is provided directly to one input of a control logic circuit 178 and through a one and a half microsecond monostable multivibrator (one shot) 180 to another input of control logic 178. In addition, the nine bit address bus VADDR (0–9) and sixteen bit data bus DTB (0–15) from CPU 62 are provided to inputs of control logic circuit 178. Control logic circuit 178 provides the S/H, ASA (0–3), ASTR, OPEN and CLOSE signals to the analog signal processors 48, 50, 52, 54, 56, 58 and 60 upon a recognition of a valid TRIG signal.

At the point in time one of the ADCBUS signals is provided, it is stored in sample and hold circuit 182 in response to an enable signal from control logic circuit 178. Thereafter, the stored analog signal is provided to an analog to digital convertor (ADC) 184 and converted to a sixteen bit digital signal. The digital signal from analog to digital convertor 184 is provided to CPU interface circuit 186 and transmitted over a serial data link to CPU 62.

Generally, there are many various purposes for data acquisition logic 64. First, data acquisition logic 64 detects the initializing of an event, that is, when a cell is properly positioned in detection station 20 and ready for identification. Further, it detects the occurrence of missed events which occur when both sample and hold circuits 138 and 146 are holding data. In addition, data acquisition logic 64 sequences the analog signal processors 48, 50, 52, 54, 56, 58 and 60 to acquire the data over the ADCBUS line upon the occurrence-of an event and digitizes the event data obtained from the analog signal processors 48, 50, 52, 54, 56, 58 and 60 and transmits it to CPU 62. In addition, it receives and transmits the various operating parameters to and from the analog signal processors 48, 50, 52, 54, 56, 58 and 60. Data acquisition logic 64 can also provide other functions beyond the scope of the subject invention, such as transmitting data to a display unit, marking the data with a time stamp and providing a count rate meter function.

The functions of data acquisition logic 64 are performed under the control of control logic 178, which can consist of either digital logic circuits, various programmable logic array modules, or one or more microprocessors. The particular implementation is within the state of the art given the following description of the functions to be performed. First, data acquisition logic 64 monitors the TRIG line from a selected one of the analog signal processors 48, 50, 52, 54, 56, 58 and 60 and compares it with the analog output of digital to analog convertor 176. When the magnitude of the TRIG signal exceeds the value of the digital to analog convertor 176 signal, an event procedure is initiated. Thus, the combination of comparator 174 and digital to analog convertor 176 are the system discriminator 67 which provides a signal manifesting that the magnitude of the selected TRIG signal is above a certain threshold programmed into digital to analog convertor 176 by CPU 62.

Generally, the output from comparator 174 is provided to trigger a one and a half microsecond monostable multivibrator (one shot) 180 and the output of multivibrator 180 is ORed with the output of comparator 174 by control logic 178, which initiates a pulse capture sequence, if one is not already occurring due to a previous detected event. The logic combinations of control logic 178, multivibrator 180 and comparator 174, together with a timer internal to control logic 178, manifest an event window. The event window can be as short as eight and one half microseconds and as long as necessary to capture a wide, or double cell, up to some finite maximum time. The rising and falling edges of the event window are determined by the initiation of an OPEN and a CLOSE signal at times determined to be able to capture the entire DPULSE delayed pulse on each of analog signal processors 48, 50, 52, 54, 56, 58 and 60. The leading edge of the OPEN signal, which starts the event window, thus occurs at a time before the DPULSE delayed pulse has entered gate 130 and the leading edge of the CLOSE signal, which ends the event window, thus occurs as near as possible following the time the DPULSE delayed pulse signal completes its passage through gate 130.

After the S/H signal is issued, control logic 178 requests that a digitalization cycle occur, if analog to digital convertor 184 is not already busy converting data from a prior event. If analog to digital convertor 184 is busy with data from a prior event, logic 178 waits until the prior event data is fully digitized and transmitted before issuing the S/H signal. In addition, analog to digital convertor 184 can also monitor various system parameters, such as sample or sheath pressure, laser operating parameters, and so forth, and provide this information between detected events when it is not busy. Once the analog event data is digitized by analog to digital convertor 184, it is transmitted by CPU interface logic to CPU 62 over a conventional serial link, such as the ones used in conventional computer networks.

Referring now to FIG. 9, a block diagram of CPU 62 is shown. CPU 62 is actually two different types of computers. It includes a conventional personal computer 188, which interfaces with conventional input/output (I/O) apparatus 42, such as keyboard, display or printer units. The other computer is pipeline network 190, which includes four processor stages 192, 194, 196 and 198 each connected together through a high speed, bidirectional serial link. Each processor stage 192, 194, 196 and 198 can be models 400 Transputer, available from INMOS, a division of S.G.S. Thompson Microelectronics, of Garland, Tex. The final processor stage 198 is also connected to personal computer 188 by a serial to parallel conversion link. The VADDR (0-8) and DTB (0-16) address and data bus signals are provided from second processor stage 194 to control logic 178 as a manifestation that first stage 192 is available to receive additional data from analog to digital convertor 184 through interface logic 186. Generally, each stage 192, 194, 196 and 198 of pipeline network 190 is programmed to perform one or more functions required as a part of the analysis of the data provided thereto from CPU interface logic 186. Once that function is completed, data is provided over the high speed serial link to the next higher stage.

In this regard, pipeline network 190 is similar in function to a pipeline computer architecture. It permits data from multiple events to be processed at the same time, such that the higher stages can be processing data from an earlier event, while the lower stages are processing data from a later event. Alternatively, more stages, or more powerful stages can be utilized to permit the data from more than two events to be analyzed at the same time.

Figure 10:
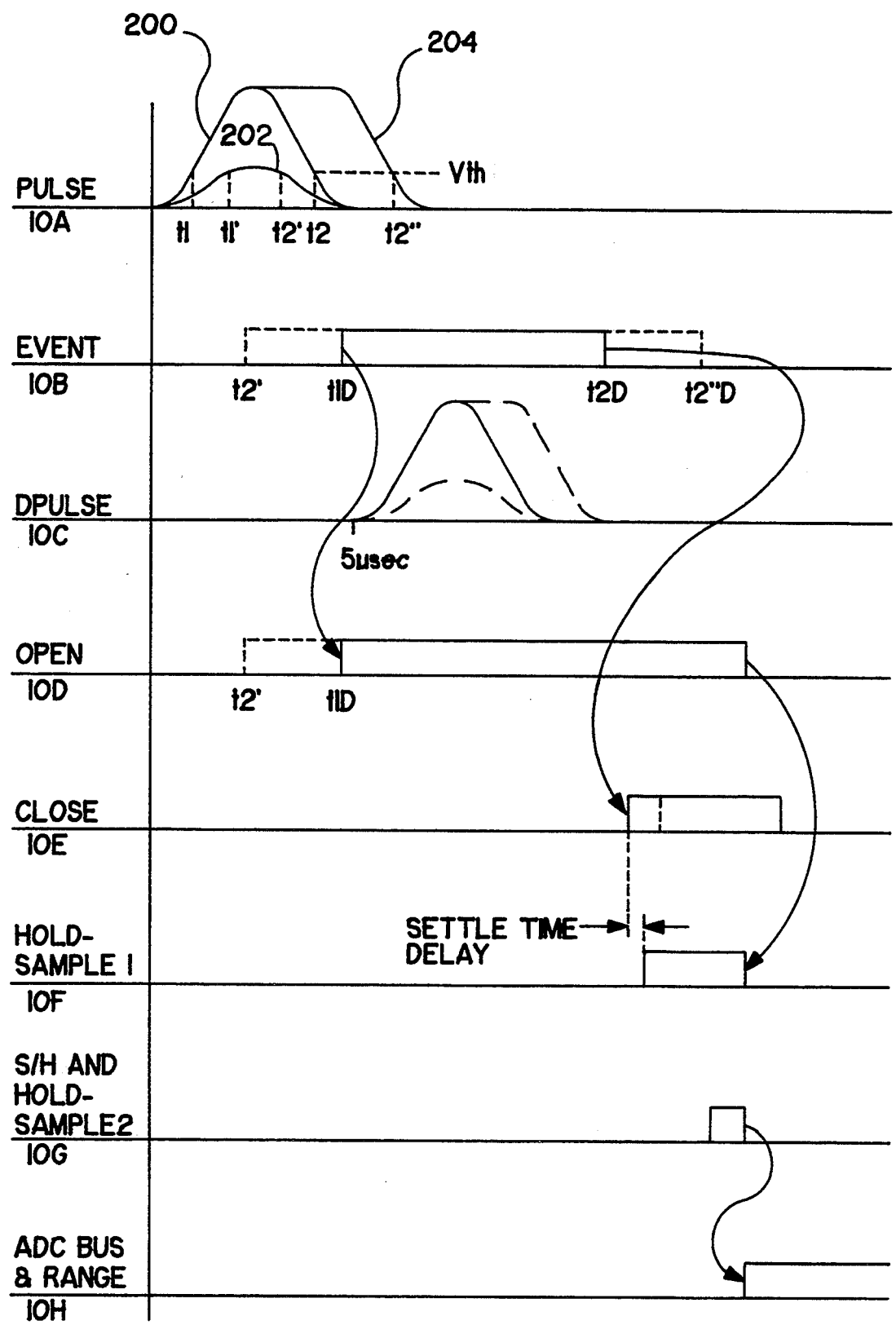
FIG. 10 shows a series of signal diagrams useful in understanding certain operational aspects of the invention.

Referring now to FIG. 10, a series of signal diagrams, labeled as FIG. 10A through FIG. 10H, are shown which are useful in understanding the operation of the circuits shown in FIGS. 5 through 9. Referring first to FIG. 10A, the PULSE signal appearing at the output of amplifier 122 in FIG. 5 is shown. A normal PULSE signal is shown by waveform 200 and appears as a Gaussian pulse manifesting the light observed from the pulse as it traverses detection station 20. As seen, the maximum value of the normal PULSE signal waveshape 200 is substantially above a threshold voltage $V_{th}$ which is the voltage value provided by programmable digital to analog convertor 176. However, for very small cells, the waveshape of the PULSE signal appears as waveshape 202, and its peak magnitude is only slightly above the threshold voltage $V_{th}$; further, the time that waveshape 202 is above $V_{th}$ is relatively short compared to the time waveshape 200 is above $V_{th}$. In some instances, two cells can stick together and cause the PULSE signal to have a longer duration, as seen by waveshape 204.

The TRIG signal applied to data acquisition logic 64 from a selected analog signal processor 48, 50, 52, 54, 56, 58 or 60, usually analog signal processor 48, is the PULSE signal for that analog signal processor, and as it rises above the $V_{th}$ value at time $t_1$, the signal from comparator 174 switches states. Control logic 178 then responds to the state change and sets a timer to effectively measure the duration of the comparator 174 signal. The purpose of measuring the duration of the comparator 174 signal is to define an event time or window, shown in FIG. 10B, during which the delayed pulse signal DPULSE, shown in FIG. 10C, will always be occurring. For normal pulses, such as waveform 200, the event time begins at time $t_{1D}$, a certain fixed delay time after time $t_1$. The delay is selected to be slightly less than the five microsecond delay provided by delay 128 and monostable multivibrator 180 in order to insure the window precedes the DPULSE signal rise. However, for short pulses, merely setting the event time a fixed delay after comparator 174 changes states can lead to problems. Specifically, for a normal waveform 200, the threshold cross-over time is designated as time $t_1$ and the for low magnitude waveform 202, the threshold cross-over time is designated as time $t_{1'}$.

In order to minimize the event duration for when a normal pulse 200 is present, the delay time between $t_1$ and $t_{1D}$ is selected to be five microseconds, less one half of the time of a normal pulse, plus some margin of error so as to be reasonably safe. However, if the same delay were added to time $t_{1'}$, the event cycle could begin after the DPULSE pulse (seen in FIG. 10C) begins increasing. Accordingly, if the time that the PULSE signal is above the threshold value $V_{th}$ is less than a certain minimum time, the event is defined to begin at some earlier time $t_{2'}$, which is a small fixed delay after the low magnitude PULSE signal falls below the threshold value $V_{th}$. A certain delay time following the time that the PULSE signal falls below the threshold value, at time $t_{2'}$, $t_2$ or $t_{2''}$, the event is considered as ended. The delay time is picked to assure that the entire event is captured.

The OPEN command signal, seen in FIG. 10D, is generated by control logic 178 a short delay time following the beginning of the event window. From this signal, the GATE signal is issued by gate logic 164 to permit the delayed pulse signal DPULSE to pass through switch 130 and be captured by either integrator 134 or peak detect circuit 132. When the event window closes at times $t_{2'}$, $t_2$ or $t_{2''}$, the CLOSE command, seen in FIG. 10E, is generated by control logic 178. The CLOSE signal, causes the GATE signal to change so that switch 130 is opened and no further signal is integrated or peak detected. The CLOSE signal also enables PLA 162 and a slight delay time after the CLOSE signal is provided, the HOLDSAMPLE1 signal is issued, as seen in FIG. 10F. In this instance, the delay is determined by delay 170 and is sufficient to permit voltages stored in the integrator 134 or peak detector 132 capacitors to settle to constant voltages after the CLOSE signal. A short delay time later, as determined by delay 171, the HI/LO signal is generated by PLA 162 to select one of the amplifiers 140 or 142. In response to the latched X32/X1 signal and after the polling commences, PLA 162 generates the RANGE signal, shown in FIG. 10H.

At some point after the CLOSE command is first issued by control logic 178, control logic 178 issues the S/H command to all of the analog signal processors 48, 50, 52, 54, 56, 58 and 60, at a time when analog to digital converter 184 is available to receive data. The issuance of the S/H signal by control logic 182 results in the issuance of the HOLDSAMPLE2 signal from inverter 168, which in turn, causes sample and hold circuit 146 to commence holding the voltage provided thereto from the selected one of amplifiers 140 or 142, as determined by the HI/LO signal. After the S/H signal is provided, the OPEN signal is reset. This, in turn, causes gate logic 164 to send the IRESET and PRESET signals to reset integrator 134 or peak detector 132. The resetting of the OPEN signal also causes the HOLDSAMPLE1 signal to return to the sample state, whereby sample and hold circuit 138 is available to accept new data. Thereafter the CLOSE signal is deactivated and gate 130 is enabled. At this point in time, sample and hold circuit 146 contains the data to be sent to data acquisition circuit 64 and sample and hold circuit 138 is available to receive data when a new cell is detected as ready to be identified.

Thereafter, data acquisition logic 62 polls the seven analog signal processor 48, 50, 52, 54, 56, 58 and 60, one at a time, and receives and digitizes the voltages stored by each sample and hold circuit 146, as well as the associated RANGE signal, which is latched in PLA 168. As the data is received, it is converted to digital data and transmitted to CPU 62 for further processing. Because CPU 62 contains multiple serial processors 192, 194, 196 and 198, each can be arranged to process different portions of successive data sets, representing successive cells.

The pipelining effect permitted by having two sample and hold circuits 138 and 146, together with the pipelining architecture of the digital processors 192, 194, 196 and 198 permits significant high flow rates through detection station 20. This is important because the cells being detected enter detection cell 20 at an asynchronous rate, and thus, the system throughput is limited by the closest random asynchronous cell spacing. Thus, it is not sufficient to merely provide the digital pipelining computer architecture because the random event spacing limits the availability of the analog portion of the cell detection, as well.

As noted above, the data presented to data acquisition logic 64 from each analog signal processor 48, 50, 52, 54, 56, 58 and 60 includes both the analog voltage held by sample and hold circuit 146 and the RANGE signal manifesting whether that voltage had been amplified by a gain of one or thirty-two. Analog to digital converter 184 is capable of providing only sixteen bits of digital data as a manifestation of the voltage being digitized. However, where the input voltages are provided over a four decades range, as is the case with the signals provided from detectors 28, 30, 32, 34, 36 and 38 to analog signal processors 48, 50, 52, 54, 56, 58 and 60, twenty bits is needed to obtain acceptable resolution over this large range for contiguous histogram data. To overcome the sixteen bit limitations of analog to digital converter 184 in the lower decades, the analog voltage is converted to a fifteen bit code and the RANGE signal is carried as the sixteenth bit. Because when the RANGE bit is set, it manifests the use of amplifier 142 having a gain of thirty-two, the sixteenth bit represents a multiplier of $2^5$; this multiplier, together with the remaining fifteen bits gives a range of twenty bits with a resolution of fifteen bits.

If a constant voltage were used as the reference voltage for comparator 145, the histogram display of the data would contain a distortion, such as a spike or gap, at the reference voltage value. While this distortion can be eliminated by careful calibration, it is still susceptible to thermal drift and eventually can appear. By providing the variable voltage from sawtooth generator 147, the point of the crossover distortion varies over a wide range and becomes much less susceptible to the effects of thermal drift. The use of sawtooth circuit 147 does not alter the data being presented, since the data is accurate, whether it is multiplied by thirty-two with the RANGE signal set, or multiplied by one with the RANGE signal not set.

While flow cytometer 10 has been described above with respect to the detection and analysis of blood cells, it is to be understood that it can be used to detect any type of small particles, such as the particles found in polluted water.

The embodiments of the invention in which an exclusive property or privilege is claimed are defined as follows:

1. A flow cytometer for detecting and identifying particles in a fluid, said flow cytometer having means for moving said particles to a detection station, means for directing energy at said detection station so that said particles intersect said energy when at said detection station, and a plurality of detectors for providing analog electric signals manifesting different results of each particle intersecting said energy, said flow cytometer comprising:
   a plurality of analog signal processors, each responsive to only one detector signal for processing, delaying and storing analog data manifesting the signal provided thereto;
   first controller means responsive to a trigger signal from a selected one of said analog signal processors for determining that a particle is intersecting said energy, said trigger signal being time related to the signals from said detectors, said first controller means providing signals to each of said analog signal processors for causing the storage of a delayed version of the signal applied thereto;
   second controller means for polling each of said plurality of analog signal processors to receive and digitize said delayed signal stored thereby and to further process said received and digitized signals in order to identify said detected particle and each analog signal processor stores a signal related to the signal provided thereto, and provides a data signal to said second controller means in response to a poll signal therefrom, each analog processor including amplifying means for amplifying each stored signal to provide said data signal, said amplifying means amplifying said stored signal with one of a first gain or a second gain, said second gain being greater than said first gain, said amplifying means amplifying said stored signal with said second gain unless the signal value amplified with said second gain exceeds a certain value.

2. The flow cytometer according to claim 1 wherein each of said analog signal processors has first and second analog signal storage means, said first storage means storing data related to said delayed signal and said second storage means storing data related to the data stored by said first storage means during the time said second controller means polls each analog signal processor.

3. The flow cytometer according to claim 2 wherein said first storage means is enabled to store data from a newly detected particle after the data previously stored thereby has been stored in said second storage means.

4. The flow cytometer according to claim 1 wherein each analog signal processor provides an associated control signal to said second controller means manifesting the one gain of said amplifying means for the data signal being provided.

5. The flow cytometer according to claim 4 wherein said second controller means includes an analog to digital converter for converting the analog signal provided thereto to a digital signal, said second controller means digital signal being limited to N bits, at least one of which is said control signal and the remaining ones of which contain the digital signal from said analog to digital converter.

6. The flow cytometer according to claim 5 wherein each of said analog signal processors has first and second analog signal storage means, said first storage means storing data related to said delayed signal and said second storage means storing data related to the data stored by said first storage means during the time said second controller means polls each analog signal processor.

7. The flow cytometer according to claim 6 wherein said signal provided for storage to said second storage means is amplified by said amplified means.

8. The flow cytometer according to claim 1 wherein each of said analog signal processors has first and second analog signal storage means, said first storage means storing data related to said delayed signal and said second storage means storing data related to the data stored by said first storage means during the time said second controller means polls each analog signal processor.

9. The flow cytometer according to claim 8 wherein said signal provided for storage to said second storage means is amplified by said amplified means.

10. A flow cytometer for detecting particles in a fluid and determining information regarding said particles, said flow cytometer having means for moving said particles to a detection station, means for directing energy at said detection station so that said particles intersect said energy when at said detection station, and detector means for providing an electric signal manifesting the result of each particle intersecting said energy, said flow cytometer further having a detection circuit comprising:
   means for detecting the presence of a particle in said detection station and providing an electric signal manifesting a parameter of said detected particle;
   first storage means for storing an electric signal related to said detector means signal after said means for detecting has detected a particle in said detection station;
   second storage means for storing, on command, an electric signal related to the signal stored by said first storage means;
   processor means responsive to the electric signal stored by said second storage means for processing the electric signal stored by said second storage means to obtain the information regarding each particle;
   command means for enabling said second storage means to store said electric signal related to the signal stored by said first storage means after said processor means has completed processing the electric signal previously stored by said second storage means and said means for detecting has detected the presence of another particle in said detection station, said command means further resets said first storage means after enabling said second storage means to store said electric signal related to the signal stored by said first storage means and said command means detects the time of occurrence of a particle entering said detection station in response to said detector means signal applied thereto; and said flow cytometer further includes delay means for delaying said detector means signal by a delay time prior to said first storage means.

11. The flow cytometer according to claim 10 wherein said delay means signal is processed and provided to said first storage means at a first time, less than said delay time, after detecting the time of occurrence of a particle entering said detection station.

12. The flow cytometer according to claim 11 wherein said command means detects the time of occurrence of a particle leaving said detection station in response to said detector means signal applied thereto, and enables said first storage means to store said processed delay means signal at a second time, greater than said delay time, following the detection of said particle leaving said detection station.

13. The flow cytometer according to claim 12 wherein said delay means signal is processed such that the time domain integral is stored in said first storage means.

14. The flow cytometer according to claim 12 wherein said delay means signal is processed such that the peak value thereof is stored in said first storage means.

15. The flow cytometer according to claim 10 wherein said command means includes threshold means to which said detector means signal is provided, said threshold means providing a first signal after said detector means signal exceeds a threshold value and a second signal after said detector means signal falls below said threshold value, said first signal being provided to permit further processing of said delay means signal prior to storage in said first storage means and said second signal being provided to enable said first storage means to store said processed delay means signal.

16. The flow cytometer according to claim 15 wherein said delay means signal occurs between said first and second signals.

17. The flow cytometer according to claim 15 wherein said threshold means determines the time that said detector means signal is above said threshold, said first signal being provided at a time, related to said delay time, after said detector means signal exceeds said threshold if said time that said detector means signal is above said threshold exceeds a certain minimum time and said first signal being provided at a time related to the time said detector means signal falls below said threshold if said time that said detector means signal is above said threshold does not exceed said certain minimum time.

18. The flow cytometer according to claim 15 wherein said threshold means provides said second signal a fixed time after said detector means signal falls below said threshold, said delay means signal occurring between said first and second signals.

19. The flow cytometer according to claim 18 wherein said delay means signal is processed such that the time domain integral is stored in said first storage means.

20. The flow cytometer according to claim 18 wherein said delay means signal is processed such that the peak value thereof is stored in said first storage means.

21. The flow cytometer according to claim 10, wherein said processor means includes a plurality of analog signal processors and each analog signal processor stores a signal related to the signal provided thereto, and provides a data signal to said second controller means in response to a poll signal therefrom, each analog processor including amplifying means for amplifying each stored signal to provide said data signal, said amplifying means amplifying said stored signal with one of a first gain or a second gain, said second gain being greater than said first gain, said amplifying means amplifying said stored signal with said second gain unless the signal value amplified with said second gain exceeds a certain value.

22. The flow cytometer according to claim 21 wherein each analog signal processor provides an associated control signal to said second controller means manifesting the one gain of said amplifying means for the data signal being provided.

23. The flow cytometer according to claim 22 wherein said second controller means includes an analog to digital converter for converting the analog signal provided thereto to a digital signal, said second controller means digital signal being limited to N bits, at least one of which is said control signal and the remaining ones of which contain the digital signal from said analog to digital converter.

24. The flow cytometer according to claim 23 wherein each of said analog signal processors has first and second analog signal storage means, said first storage means storing data related to said delayed signal and said second storage means storing data related to the data stored by said first storage means during the time said second controller means polls each analog signal processor.

25. The flow cytometer according to claim 24 wherein said signal provided for storage to said second storage means is amplified by said amplified means.

26. The flow cytometer according to claim 21 wherein each of said analog signal processors has first and second analog signal storage means, said first storage means storing data related to said delayed signal and said second storage means storing data related to the data stored by said first storage means during the time said second controller means polls each analog signal processor.

27. The flow cytometer according to claim 26 wherein said signal provided for storage to said second storage means is amplified by said amplified means.

28. A flow cytometer for detecting and identifying particles in a fluid, said flow cytometer having means for moving said particles to a detection station means for directing energy at said detection station so that said particles intersect said energy when at said detection station, and a plurality of detectors for providing analog electric signals manifesting different results of each particle intersecting said energy, said flow cytometer comprising:

a plurality of analog signal processors, each responsive to one detector signal, each analog signal processor having delay means for providing a delayed signal, which is delayed version of that one detector means signal, first storage means for storing a processed version of said delayed signal, and second storage means for storing, on command, an electric signal related to the signal stored by said first storage means;

first controller means responsive to the detector means signal from a selected one of said analog signal processors for determining that a particle is intersecting said energy, said first controller means providing signals to each of said analog signal processors for causing the further processing of said delayed signal and the storage in said first storage means of a value related to said processed delayed signal, and second controller means for providing signals to each of said analog signal processors to cause a value related to the value stored in said first storage means to be stored in said second storage means, said second controller polling each of said analog signal processors to receive, digitize and further process signals related to the values stored in each of said second storage means in order to identify said detected particle, said second controller means providing signals to each of said analog signal processors to cause said value related to the value stored in said first storage means to be stored in said second storage means after completing the polling each of said analog signal processors, said first controller means being disabled from determining that a particle is intersecting said energy until said second controller means provides said signals to each of said analog signal processors causing said value related to the value stored in said first storage means to be stored in said second storage means.

29. The flow cytometer according to claim 28 wherein said first controller means is enabled to detect a detector means signal during the time said second controller means is polling each of said analog signal processors.

30. The flow cytometer according to claim 29 wherein the further processing of said delayed signal is determining the time domain integral thereof.

31. The flow cytometer according to claim 30 wherein the further processing of said delayed signal is determining the maximum value thereof.

32. The flow cytometer according to claim 29 wherein said second controller means provides signals to each of said analog signal processors to cause said value related to the value stored in said first storage means to be stored in said second storage means after completing the polling each of said analog signal processors, said first controller means being disabled from determining that a particle is intersecting said energy until said second controller means provides said signals to each of said analog signal processors causing said value related to the value stored in said first storage means to be stored in said second storage means.

33. The flow cytometer according to claim 28 wherein said first controller means includes threshold detector means for determining when and how long said detector means signal from said selected one of said analog signal processors exceeds a threshold value.

34. An apparatus for detecting particles said apparatus having means for moving said particles to a detection station, means for directing energy at said detection station so that said particles intersect said energy when at said detection station, and detector means for providing an analog electric signals manifesting a result of each particle intersecting said energy, said detector means signals varying in magnitude over a certain range, said particle detecting apparatus further having converter means for converting an analog electric signal applied to an input thereof to a digital signal, said convertor means having a certain number, n, of digital outputs for manifesting the digital value of the analog signal provided to said converter means input, the improvement comprising:

first and second amplifiers each responsive to said detector means signal, said first amplifier having a first gain and said second amplifier having a second gain, said second gain being greater than said first gain;

switch means having a pair of inputs, each connected to a different one of said first and second amplifiers, and an output switchably connected with one of said inputs in response to a switch signal provided to said switch means, a switch means output signal appearing at said output;

means for determining whether said second amplifier signal exceeds a certain value and for providing said switch signal to said switch means to connect said output with said first input whenever said second amplifier signal exceeds said certain value and to connect said output with said second input whenever said second amplifier signal does not exceed said certain value, said certain value varying in magnitude with respect to time; and said switch means output signal being coupled to said converter means input for conversion by said converter means to a digital signal manifested in n-m of said converter digital outputs, where m is at least one, said switch signal being contained in the remaining converter means digital outputs.

35. The improvement according to claim 34 wherein m equals one.

36. The improvement according to claim 34 wherein said means for determining is a comparator.

37. The improvement according to claim 36 wherein said comparator has a reference input and a data input, the output of said second amplifier means being coupled to said data input and a signal having a magnitude varying with time being coupled to said reference input.

38. The improvement according to claim 37 wherein said switch means output signal and switch signal are stored and thereafter provided to said convertor means upon request of said converter means.

39. The improvement according to claim 38 wherein m equals one.

40. The improvement according to claim 38 wherein said apparatus for detecting particles further identifies the detected particles and displays information regarding said identified particles as a histogram.

41. The improvement according to claim 34 wherein said certain value varies in magnitude with respect to time.

42. A flow cytometer for detecting and identifying various types of particles in a particle containing flowing fluid comprising:

means for causing said fluid to flow through a detection station through which is directed energy;

a plurality of detector means, each for detecting a different responses of each particle to said energy, each of said detector means providing an electric signal manifesting one response, and each electric signal having an amplitude which varies as a result of the particle type;

analog to digital converter means for responding to signals provided thereto for providing a digital signal of n bits manifesting the digital value of an analog signal provided thereto; and a signal processor for each detector means responsive to that detector means signal for making available an analog signal for provision to said analog to digital converter means, each processor including, first and second amplifiers each responsive to the detector means signal provided to that signal processor, said first amplifier having a first gain and said second amplifier having a second gain;

said second gain being greater than said first gain;

means for determining whether or not said second amplifier signal exceeds a certain value and for providing a switch signal manifesting that said second amplifier signal exceeds said certain value, said means for determining is an analog comparator having a reference voltage input to which a reference voltage is applied to manifest said certain value, said analog comparator further having a signal input coupled to said second input of said switch means, said analog comparator providing a signal manifesting whether or not the voltage at said signal input is greater than said reference voltage and said reference voltage is time varying between a first and second amplitude; and switch means having a pair of inputs, each connected to a different one of said first and second amplifiers, and an output switchably connected with said first input in response to said switch signal manifesting that said second amplifier signal exceeds said certain value, and with said second input in response to said switch signal manifesting that said second amplifier signal does not exceed said certain value, a switch means output signal appearing at said output;

means for coupling said switch means output signal and said switch signal from each signal processor, one at a time, to said analog to digital converter means, said analog to digital converter means converting each coupled switch means output signal to a digital signal manifested in $n-1$ bits, said analog to digital converter means further including the manifestation of said switch signal as the remaining bit of each analog to digital converter means digital signal; and means responsive to said analog to digital converter means digital signals for identifying each detected particle.

43. The flow cytometer according to claim 42 wherein said reference voltage is a sawtooth wave.

44. The flow cytometer according to claim 43 wherein means for identifying includes displaying each identified cell in a histogram format.

45. The flow cytometer according to claim 42 wherein said certain value varies with time.

46. The flow cytometer according to claim 45 wherein means for identifying includes displaying each identified cell in a histogram format.

* * * * *